United States Patent
Masuda et al.

(10) Patent No.: US 9,527,836 B2
(45) Date of Patent: *Dec. 27, 2016

(54) CRYSTAL HAVING SPECIFIC CRYSTAL HABIT AND PHARMACEUTICAL COMPOSITION CONTAINING THE CRYSTAL AS ACTIVE INGREDIENT

(71) Applicants: POLA PHARMA INC., Tokyo (JP); NIHON NOHYAKU CO., LTD., Tokyo (JP)

(72) Inventors: Takaaki Masuda, Kanagawa (JP); Makoto Gotoh, Tokyo (JP); Hideo Kaneda, Tokyo (JP)

(73) Assignees: POLA PHARMA INC., Tokyo (JP); NIHON NOHYAKU CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,864

(22) PCT Filed: Apr. 11, 2014

(86) PCT No.: PCT/JP2014/060993
§ 371 (c)(1),
(2) Date: Feb. 5, 2015

(87) PCT Pub. No.: WO2015/033612
PCT Pub. Date: Mar. 12, 2015

(65) Prior Publication Data
US 2016/0168136 A1 Jun. 16, 2016

(30) Foreign Application Priority Data
Sep. 6, 2013 (JP) .................. 2013-185313

(51) Int. Cl.
C07D 409/06 (2006.01)
A61K 31/4178 (2006.01)
A61K 9/00 (2006.01)
A61K 47/26 (2006.01)

(52) U.S. Cl.
CPC ........... *C07D 409/06* (2013.01); *A61K 9/0034* (2013.01); *A61K 31/4178* (2013.01); *A61K 47/26* (2013.01)

(58) Field of Classification Search
None
See application file for complete search history.

(56) References Cited

U.S. PATENT DOCUMENTS

| 5,900,488 A | 5/1999 | Kodama et al. |
| 9,012,484 B2 * | 4/2015 | Masuda ............. A61K 31/4178 514/397 |
| 9,199,977 B2 * | 12/2015 | Masuda ............... C07D 409/06 |
| 2002/0048610 A1 | 4/2002 | Cima et al. |
| 2003/0162226 A1 | 8/2003 | Cima et al. |
| 2005/0191614 A1 | 9/2005 | Cima et al. |
| 2009/0030059 A1 | 1/2009 | Miki et al. |
| 2009/0076109 A1 | 3/2009 | Miki et al. |
| 2009/0137651 A1 | 5/2009 | Kobayashi et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0249202 A1 | 9/2010 | Koga et al. |
| 2012/0015997 A1 | 1/2012 | Miki et al. |
| 2012/0022120 A1 | 1/2012 | Kobayashi et al. |
| 2012/0149745 A1 | 6/2012 | Kobayashi et al. |
| 2012/0329845 A1 | 12/2012 | Masuda et al. |
| 2013/0011351 A2 | 1/2013 | Kobayashi et al. |
| 2013/0090365 A1 | 4/2013 | Kubota et al. |
| 2013/0096187 A1 | 4/2013 | Kobayashi et al. |
| 2014/0080882 A1 | 3/2014 | Masuda et al. |

FOREIGN PATENT DOCUMENTS

| CN | 103012385 A * | 4/2013 |
| CN | 103012385 A | 4/2013 |
| EP | 0715856 A1 | 6/1996 |
| EP | 2005958 A1 | 12/2008 |
| JP | 09-100279 A | 4/1997 |

(Continued)

OTHER PUBLICATIONS

English Translation of CN 103012385-A, 2013.*
U.S. Appl. No. 13/988,003, Masuda.
U.S. Appl. No. 14/263,293, Masuda et al.
U.S. Appl. No. 14/347,939, Masuda et al.
U.S. Appl. No. 14/358,709, Masuda et al.
U.S. Appl. No. 14/388,218, Masuda et al.
U.S. Appl. No. 14/592,695, Masuda et al.
International Search Report and Written Opinion of the International Searching Authority for International Application No. PCT/JP2014/060993, mailed on Jul. 15, 2014.
Niwano et al, "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

(Continued)

*Primary Examiner* — Samantha Shterengarts
(74) *Attorney, Agent, or Firm* — Knobbe, Martens, Olson & Bear, LLP

(57) ABSTRACT

An object is to provide a crystal having a new crystal habit of luliconazole and expand the possibility of application to pharmaceuticals. Disclosed is a crystal of luliconazole having such a crystal habit that (020) plane is a specific crystal growth surface.

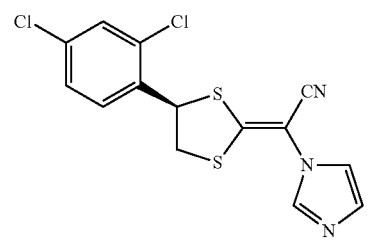

luliconazole

13 Claims, 1 Drawing Sheet

(56) References Cited

FOREIGN PATENT DOCUMENTS

| | | |
|---|---|---|
| JP | 2002-114680 A | 4/2002 |
| JP | 2003-519698 A | 6/2003 |
| WO | WO 2007/102241 | 9/2007 |
| WO | WO 2007/102242 | 9/2007 |
| WO | WO 2007/102243 | 9/2007 |
| WO | WO 2009/031642 | 3/2009 |
| WO | WO 2009/031643 | 3/2009 |
| WO | WO 2009/031644 | 3/2009 |
| WO | WO 2010/117089 | 10/2010 |
| WO | WO 2010/117091 | 10/2010 |
| WO | WO 2014/041708 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/115487 A1 | 7/2014 |
| WO | WO 2014/115488 A1 | 7/2014 |
| WO | WO 2014/136282 | 9/2014 |
| WO | WO 2014/185542 A1 | 11/2014 |

OTHER PUBLICATIONS

Office Action issued in corresponding Japanese Patent Application No. 2013-185313 on Sep. 24, 2014, with verified English translation.

Office Action issued in corresponding Japanese Patent Application No. 2015-000723, on May 12, 2015.

Chozaigaku -Kiso to Oyo- (dispensing pharmacy—Basics and Practical Guide), published by Nanzando Co., Ltd., p. 142-145 (Sep. 20, 1977).

Jikkenkagakukoza Zoku 2 (Experimental Chemistry Second series 2), Separation and Purification, published by Maruzen Co., Ltd., p. 159-178, 186-187 (Jan. 25, 1967).

Shin-Yakuzaigakusoron (New General Pharmaceutics) ($3_{rd}$ Edition), published by Nankodo Co., Ltd., p. 111 (Apr. 10, 1987).

Shinseizaigaku (New Pharmaceutics), published by Nanzando Co., Ltd., p. 102-103, 232-233 (Apr. 25, 1984).

U.S. Appl. No. 14/427,890, Masuda et al.

\* cited by examiner

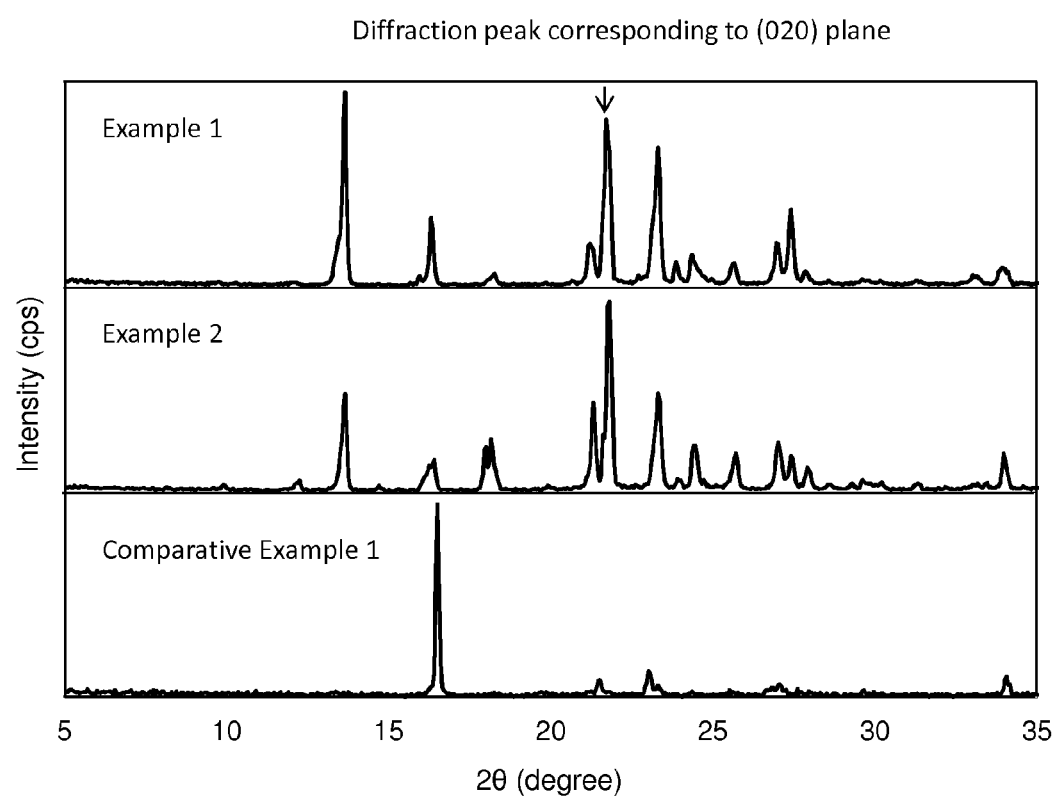

US 9,527,836 B2

CRYSTAL HAVING SPECIFIC CRYSTAL HABIT AND PHARMACEUTICAL COMPOSITION CONTAINING THE CRYSTAL AS ACTIVE INGREDIENT

CROSS-REFERENCE TO RELATED APPLICATIONS

This application is the U.S. National Phase under 35 U.S.C. §371 of International Application PCT/JP2014/060993, filed Apr. 11, 2014, which claims priority to JP 2013-185313, filed Sep. 6, 2013.

TECHNICAL FIELD

The present invention relates to a crystal having a useful crystal habit of luliconazole as an active ingredient for a pharmaceutical composition, and a pharmaceutical composition which comprises the crystal as the active ingredient.

BACKGROUND ART

Luliconazole is an antifungal agent which is excellent in the action on fungi. At present, luliconazole is widely used as a pharmaceutical or medicine for tinea pedis and tinea corporis, and it is going to be applied for the action on tinea unguium. In relation to the pharmaceutical preparation (medicament preparation) of luliconazole, those known as problems to be solved include, for example, the stereoisomerization to form, for example, the SE isomer or the Z isomer, and the crystal deposition caused immediately after the application (see, for example, Patent Documents 1 to 6). The problem of dissolution characteristics possessed by luliconazole exists on the background of the problem of the crystal deposition caused immediately after the application as described above, for which a lot of researches or studies have been made to realize pharmaceutical preparations (medicament preparations). However, not a few formulations have been rejected or unaccepted from the candidate of the pharmaceutical preparation on account of the problem of crystal deposition caused during the long-term storage of the pharmaceutical preparation system. The crystal deposition in the system is a topic concerning the effective concentration, and hence it is affirmed that the crystal deposition in the system is one of the important problems.

Further, it is also expected that luliconazole is to be applied to pneumonia and vaginitis (colpitis), without being limited to *Trichophyton*, because luliconazole has a strong antifungal action. In particular, as for these diseases, luliconazole also has an antiprotozoal effect on *Trichomonas* and luliconazole also has an effect against *Chlamydia*, which may coexist highly probably. Therefore, it is affirmed that luliconazole is expected to expand the application as compared with any other antifungal agent. In this context, it is assumed that luliconazole is to be used as a vaginal tablet or a vaginal suppository to treat vaginitis. However, in the case of the vaginal tablet, luliconazole has extremely low blending performance with respect to any aqueous carrier. Therefore, the development of any means to improve the blending performance is a great task.

On the other hand, it is known that the crystal of luliconazole is obtained by performing recrystallization from a mixture solution of ethyl acetate and n-hexane (see Patent Document 7). An investigation is also made about the crystal form of luliconazole (see, for example, Patent Document 8).

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/031642;
Patent Document 5: WO2009/031643;
Patent Document 6: WO2009/031644;
Patent Document 7: JP9-100279A;
Patent Document 8: CN103012385A.

SUMMARY OF THE INVENTION

Technical Problem

Further, the following fact has been found out according to the investigations having been hitherto performed by the present inventors. That is, the crystal system of luliconazole resides in the monoclinic crystal, but a large number of planes or surfaces exist, on which the specific growth is caused depending on the condition. There are crystals having various different crystal habits including, for example, the crystal habit in which the (11-1) plane is the specific crystal growth surface, the crystal habit in which the (021) plane is the specific crystal growth surface, and the crystal habit in which the (011) plane is the specific crystal growth surface. The following fact has been also found out. That is, the crystals, which have the different crystal habits as described above, have different physical characteristics respectively. Therefore, when the crystal habit is selected in conformity with the application, it is possible to produce a pharmaceutical composition having good usability although the component is the same. Owing to the discovery of the different crystal habits, the range of application with respect to the pharmaceutical composition is expanded, including, for example, the improvement in the medicament preparation (pharmaceutical preparation) step and the improvement in the quality of the final product. Therefore, it is demanded to discover a new crystal habit.

The present invention has been made in the circumstances as described above, an object of which is to provide a crystal having a new crystal habit of luliconazole and expand the possibility of application to pharmaceuticals or medicines.

Solution to Problem

Taking the foregoing circumstances into consideration, the present inventors have repeatedly performed diligent researches and efforts in order to seek for a crystal having a new crystal habit in order to expand the possibility of application of luliconazole to pharmaceuticals or medicines. As a result, a crystal has been found out, which has such a crystal habit that the (020) plane is the specific crystal growth surface. It is consequently estimated, for example, that such a crystal habit has a high affinity for a polar component as compared with another known crystal habit in which the (11-1) plane is the specific crystal growth surface. Thus, the invention has been consequently completed. That is, the gist or feature of the present invention is as follows.

<1> A crystal of luliconazole having such a crystal habit that (020) plane is a specific crystal growth surface:

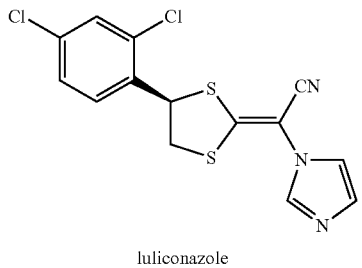 [SMILES: N#C/C(=C1/SC[C@@H](c2ccc(Cl)cc2Cl)S1)n1ccnc1]

luliconazole

<2> The crystal according to <1>, wherein:

$I_{(020)}$, which is included in $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$, takes a first place or a second place as ranked in an order starting from those having a high peak intensity; and $I_{(020)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than 20%, provided that: peak intensities of diffraction peaks, which correspond to (001) plane, (100) plane, (10-1) plane, (011) plane, (110) plane, (11-1) plane, (10-2) plane, (11-2) plane, (020) plane, (021) plane, (20-2) plane, (121) plane, (013) plane, (11-3) plane, and (221) plane, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of $2\theta=5$ to $35°$ in powder X-ray diffraction measurement in which $CuK\alpha$ is used as an X-ray source.

<3> The crystal according to <1> or <2>, wherein the crystal is a monoclinic crystal.

<4> The crystal according to any one of <1> to <3>, wherein the crystal is recrystallized from alcohol which may comprise water.

<5> A crystal of luliconazole having such a crystal habit that sulfur atom is arranged on a specific crystal growth surface.

<6> An active pharmaceutical ingredient, comprising the crystal as defined in any one of <1> to <5>.

<7> A pharmaceutical composition comprising the crystal as defined in any one of <1> to <5> or the active pharmaceutical ingredient as defined in <6> together with a component of medicament preparation.

<8> The pharmaceutical composition according to <7>, wherein a solid of the pharmaceutical composition is to be directly administered to an affected part.

<9> The pharmaceutical composition according to <7> or <8>, wherein the pharmaceutical composition is a vaginal tablet.

<10> The pharmaceutical composition according to any one of <7> to <9>, wherein saccharide is comprised as a component of medicament preparation.

<11> The pharmaceutical composition according to <10>, wherein the saccharide is lactose.

<12> A production method for producing a pharmaceutical composition, comprising a step of dissolving the crystal as defined in any one of <1> to <5> or the active pharmaceutical ingredient as defined in <6> in a polar solvent.

<13> A pharmaceutical composition produced by the production method as defined in <12>.

Advantageous Effects of Invention

According to the present invention, it is possible to provide the crystal having the new crystal habit of luliconazole and expand the possibility of application to pharmaceuticals.

BRIEF DESCRIPTION OF THE DRAWING

FIG. 1 shows results of powder X-ray diffraction measurement for crystals of the present invention and Comparative Example.

DESCRIPTION OF EMBODIMENTS (1) Crystal of Luliconazole of the Present Invention

The crystal of luliconazole of the present invention is characterized in that the crystal has such a crystal habit that (020) plane is a specific crystal growth surface. The crystal having the crystal habit as described above can be prepared by dissolving luliconazole in lower alcohol such as methanol or the like while being heated (dissolving temperature: 60 to 70° C.), adding a poor solvent, thereafter performing cooling while applying vigorous stirring, depositing the crystal, separating the crystal by means of filtration, and drying the crystal while performing blowing at a low temperature of 30 to 40° C. It is also possible to add a seed crystal upon the crystal deposition. It is also preferable for the crystallization to apply the shock to the solution, for example, such that the wall surface is rubbed. In this procedure, it is preferable that the amount of the poor solvent to be added is a volume of 10 to 60% with respect to the lower alcohol, for the following reason. That is, even when the amount of the poor solvent is either large or small, the (020) plane does not become the specific crystal growth surface in some cases. Further, as for the lower alcohol, it is preferable to use alcohol having a number of carbon atom or carbon atoms of 1 to 4, i.e., methanol, ethanol, 1-propanol (propyl alcohol), 2-propanol (isopropyl alcohol), 1-butanol (n-butyl alcohol), 2-butanol (sec-butyl alcohol), 2-methyl-1-propanol (isobutyl alcohol), and 2-methyl-2-propanol (tert-butyl alcohol). It is possible to preferably exemplify, ethanol, isopropyl alcohol, and n-butyl alcohol in addition to methanol. Alcohols as described above can be appropriately mixed with each other, and/or diethyl ether and/or diisopropyl ether can be added to regulate the solubility as well.

As for the recrystallization, the recrystallization may be performed with water-comprising alcohol, or a poor solvent may be used. The phrase "poor solvent is used" means the following fact. That is, the phrase means that an amount of water, which is sufficient for the deposition, is added to an alcohol solution of luliconazole.

The recrystallization can be performed in accordance with any ordinary recrystallization technique.

In relation to the crystal of luliconazole, the present inventors have grasped the fact that various crystals having different characteristics are obtained in accordance with the difference in the production step for producing the crystal, for example, the difference in the recrystallization solvent and the recrystallization method. Further, literatures which describe the crystal form such as Patent Document 8 described above are also present. In order to seek for the cause thereof, the present inventors have performed the recrystallization while changing the recrystallization solvent and the recrystallization method, and the present inventors have performed the powder X-ray diffraction measurement by using CuKα as an X-ray source. In relation thereto, the drawing shows a powder X-ray diffraction pattern of the crystal having such a crystal habit that (020) plane is the specific crystal growth surface, wherein it is acknowledged that the value of the characteristic peak of 2θ exists in the vicinity of 21.7°. It has been acknowledged that the peak is present at this position for the luliconazole crystal during the investigation having been hitherto performed by the present inventors. However, this peak has never appeared specifically in a large size. It has been judged that a novel crystal habit has been found out.

The specific growth surface of the crystal herein means the surface on which the growth occurs with ease as compared with other surfaces. The specific growth surface of the crystal is the surface which belongs to the peak that has a significantly large peak intensity as compared with the sum total of peak intensities of other diffraction peaks within a measured diffraction angle range when the powder X-ray diffraction measurement is performed. The specific growth surface of the crystal can be detected, for example, as the peak which specifically has the high peak intensity of the diffraction peak in the powder X-ray diffraction measurement for the crystal.

In this context, the phrase "the value of 2θ is provided in the vicinity of 21.7°" means, for example, a range of 21.7°±0.7°, preferably 21.7°±0.5°.

The phrase "peak existing in the vicinity of 21.7° is specifically large in relation to the value of 2θ" means that "$I_{(020)}$, which is included in $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$, takes a first place or a second place as ranked in an order starting from those having a high peak intensity; and $I_{(020)}$ with respect to a sum total of $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ is not less than 1/5, provided that:

peak intensities of diffraction peaks, which correspond to (001) plane, (100) plane, (10-1) plane, (011) plane, (110) plane, (11-1) plane, (10-2) plane, (11-2) plane, (020) plane, (021) plane, (20-2) plane, (121) plane, (013) plane, (11-3) plane, and (221) plane, are designated as $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ respectively". In other words, it is meant that "$I_{(020)}$, which is included in $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$, takes a first place or a second place as ranked in an order starting from those having a high peak intensity; and $I_{(020)}$ with respect to a sum total of $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ is not less than 20%". The numerical value is presented with reference to the effect of the crystal referred to in Examples described later on.

Luliconazole can be used irrelevant to the crystal system thereof, provided that the purity thereof is not less than 90% and more preferably not less than 95%, as luliconazole which is to be used to prepare the crystal having the crystal habit as described above. Luliconazole as described above can be synthesized, for example, in accordance with a method described in Japanese Patent Application Laid-open No. 60-218387. That is, 1-(cyanomethyl)imidazole and carbon disulfide are reacted to obtain a compound of (III) which is reacted with a compound of a general formula (II) having a leaving group, and thus a compound represented by a certain general formula (1) can be obtained. The compound, which corresponds to R=X=Cl and which is included in the compounds represented by the general formula (1), is luliconazole. The leaving groups Y and Y' as described above can be preferably exemplified, for example, by methanesulfonyloxy group, benzenesulfonyloxy group, p-toluenesulfonyloxy group, or halogen atom. R and X represent hydrogen atom or halogen atom.

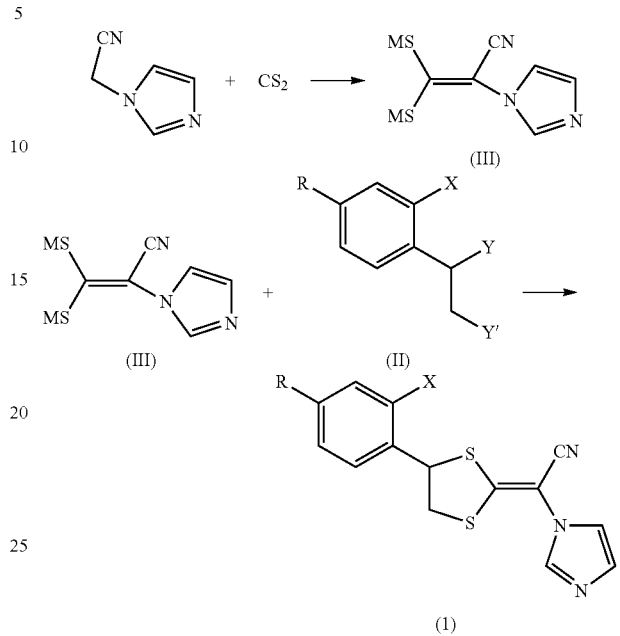

In the formulas, Y and Y' represent leaving groups, and M represents alkali metal atom.

(2) Active Pharmaceutical Ingredient of the Present Invention

The active pharmaceutical ingredient of the present invention can comprise substances, impurities, and analogs within a range of permission as the active pharmaceutical ingredient other than the crystal of luliconazole. However, it is especially preferred that the active pharmaceutical ingredient of the present invention is substantially composed of the crystal of luliconazole.

The crystal, which has the crystal habit of (020) plane as the crystal of the present invention, is estimated to be excellent in the solubility in the polar solvent such as alcohol or the like. The mechanism thereof is considered such that the molecule, which has the high affinity for the polar solvent such as chlorine atom or the like, is arranged on the contact surface of the crystal with respect to the solvent. As described later on, as for the crystal having such a crystal habit that (020) plane is the specific crystal growth surface, sulfur atom is arranged on the plane. There is such a possibility that this arrangement may contribute to the reaction even in the case of the solid state in relation to the reaction in which the sulfur atom is the active site. In this meaning, it is considered that the physiological action is different from crystals having any other crystal habit in some cases as well. For example, the addition reaction of thiol is assumed as the reaction as described above. The present inventors consider that the effect to be exerted may possibly differ depending on the crystal habit, for example, in relation to *Trichomonas* in which cysteine is an important reactive molecule. The specific surface property as described above also interacts with other pharmaceutical preparation components, which has the interaction with saccharide or sugar, especially lactose. When the active ingredient is processed into a tablet, it is possible to obtain a tablet having a high hardness. The property as described above means that a vaginal tablet having high stability is provided, which is excellent in the performance to isolate the acid component and the basic component in relation to the vaginal tablet for which a foam tablet (effervescent tablet) is assumed. As for the sugar of the pharmaceutical preparation component, it is possible to preferably exemplify glucose and sucrose other than lactose. It is also possible to use two or more of the sugars in combination.

The time, which is required for the dissolving step in the polar solvent when the crystal having such a crystal habit that (020) plane of luliconazole is the specific growth surface is used in the dissolving step, for example, when a pharmaceutical preparation having a content of luliconazole of 0.1 to 30% by mass with respect to the total amount of the pharmaceutical preparation is prepared, differs depending on, for example, the dissolving condition, depending on, for example, the content of luliconazole in the pharmaceutical preparation and the treatment condition. However, the time is approximately not more than 70%, preferably not more than 60%, and more preferably not more than 50% as compared with the time which is required for the dissolving step when the crystal having such a crystal habit that (11-1) plane is the specific growth surface is used.

The suppressing effect (suppression ratio), which is exerted on the pathogen, for example, when the crystal having such a crystal habit that (020) plane of luliconazole is the specific growth surface is used for a pharmaceutical preparation having a content of luliconazole of 0.1 to 30% by mass with respect to the total amount of the pharmaceutical preparation, differs depending on, for example, the way of measurement of the suppressing effect, depending on, for example, the content of luliconazole in the pharmaceutical preparation and the treatment condition. However, the suppressing effect (suppression ratio) may be approximately not less than 1.2 times, preferably not less than 1.3 times, and more preferably not less than 1.5 times the suppressing effect which is exerted on the pathogen when the crystal having such a crystal habit that (11-1) plane is the specific growth surface is used.

The hardness, which is obtained, for example, when the crystal having such a crystal habit that (020) plane of luliconazole is the specific growth surface is used for a pharmaceutical preparation having a content of luliconazole of 0.1 to 30% by mass with respect to the total amount of the pharmaceutical preparation, has the numerical value which varies depending on, for example, the tablet making condition, depending on, for example, the content of luliconazole in the pharmaceutical preparation and the treatment condition. However, the hardness may be approximately not less than 1.5 times, preferably not less than 2 times, and more preferably not less than 3 times the hardness which is obtained when the crystal having such a crystal habit that (11-1) plane is the specific growth surface is used.

<Peak in the Vicinity of 21.7° in Powder X-Ray Diffraction Pattern>

The crystal of the present invention is characterized by the peak provided in the vicinity of 21.7° as the value of 2θ in the powder X-ray diffraction pattern. The peak at 21.7° as the value of 2θ in the powder X-ray diffraction pattern was theoretically calculated from the single crystal X-ray diffraction data. As a result, the peak represents (020) plane. Two sulfur atoms are arranged on the plane. On the other hand, the inventors have confirmed that the crystal, which is the hitherto known crystal and which is recrystallized from n-hexane-ethyl acetate, is the crystal having such a crystal habit that (11-1) plane is the specific growth surface. Phenyl group is arranged on this plane. This plane is the plane represented by the peak provided in the vicinity of 16° as the value of 2θ in the powder X-ray diffraction measurement.

(3) Pharmaceutical Composition of the Present Invention

The pharmaceutical composition of the present invention is characterized in that the pharmaceutical composition comprises the crystal of the present invention or the active pharmaceutical ingredient of the present invention. It is estimated that the crystal as described above is excellent in the solubility in the polar solvent.

As for the production method for producing the pharmaceutical composition of the present invention, the pharmaceutical composition can be produced in the same manner as in the conventional production method for producing the pharmaceutical composition comprising luliconazole except that the crystal of the present invention or the active pharmaceutical ingredient of the present invention is comprised. It is estimated that the crystal of the present invention or the active pharmaceutical ingredient of the present invention is excellent in the solubility in the polar solvent, and the crystal of the present invention or the active pharmaceutical ingredient of the present invention is excellent in the solubility in the polar solvent such as alcohol or the like. Therefore, it is preferable to provide a pharmaceutical preparation which includes the dissolving step in the polar solvent in the production steps.

The administration form of the pharmaceutical composition of the present invention may be any one of the oral administration by using, for example, tablet, capsule, granule, powder, and syrup and the parenteral administration by using, for example, injection, preparation for external use, suppository, and transdermal absorption agent.

The agent or formulation type is not limited as well, for which it is possible to exemplify various formulation types including, for example, forms of liquid, solid, emulsion, paste, gel, powder (powdery), granule, pellet, and stick.

In the case of the use as the preparation for external use, for example, it is possible to provide the pharmaceutical preparation for external use including, for example, cream, liquid, lotion, emulsion, tincture, ointment, aqueous gel, oily gel, aerosol, powder, shampoo, soap, enamel formulation for nail application, tablet for vagina (vaginal tablet), and vaginal suppository.

The content of luliconazole is preferably 0.1 to 50% by mass and more preferably 0.5 to 15% by mass with respect to the total amount of the pharmaceutical preparation.

The pharmaceutical preparation of the present invention can be produced by performing the processing or treatment in accordance with any ordinary method while appropriately adding thereto, for example, solvent, coloring agent, antioxidant, chelating agent, emulsifier/dispersing agent, solubilizing agent, disintegrating agent, excipient, binding agent, coating agent, and taste/odor-correcting agent other than the luliconazole crystal having such a crystal habit that the (020) plane is the specific crystal growth surface. As for the especially preferred component, it is possible to preferably exemplify saccharide or sugar including, for example, glucose, sucrose, and lactose as described above. The content of the component as described above is preferably 10 to 90% by mass and more preferably 30 to 60% by mass with respect to the total amount of the pharmaceutical preparation.

The pharmaceutical composition of the present invention is preferably used to treat or cure the disease caused by any fungus or prevent the deterioration of the disease by utilizing the characteristic of luliconazole. The disease caused by any fungus can be exemplified by tinea pedis such as athlete's foot, tinea corporis such as candidiasis and tinea versicolor, and trichophytosis of hard keratin portion such as tinea unguium. It is especially preferable to use the pharmaceutical composition of the present invention for treating the disease of the hard keratin portion such as tinea unguium, because the effect thereof is remarkable. The effect of the pharmaceutical composition of the present invention is expressed on the nail especially preferably. However, the effect is also exerted on any ordinary dermatomycosis. Therefore, the pharmaceutical composition, which is directed to the dermatomycosis and which fulfills the construction of the present invention, also belongs to the technical scope of the present invention. The dermatomycosis as described above can be exemplified, for example, by the tinea pedis and the trichophytosis of the propagation in horny substance type appearing, for example, in the heel and being included in the tinea pedis. As for the dermatomycosis described above, it is preferable to make the application to the trichophytosis of the propagation in horny substance type on which any ordinary agent or drug hardly exerts the effect, because the effect of the present invention remarkably arises.

Further, it is also possible to preferably exemplify, for example, the application to vaginitis (colpitis) and pneumonia caused, for example, by fungus such as *Candida* or the like, protozoa such as *Trichomonas* or the like, and intracellular parasite such as *Chlamydia* or the like, the percutaneous administration to outer labia, the intravaginal administration, the oral administration, and the administration by injection. In the case of the administration against, for example, *Candida*, *Trichomonas*, and *Chlamydia* as described above, it is possible to especially preferably exemplify the administration to outer labia. In particular, the active pharmaceutical ingredient of the present invention has the reactivity even in the solid state. Therefore, it is preferable to apply the same to the pharmaceutical preparation including, for example, a foam vaginal tablet or effervescent vaginal tablet to be administered as the solid to the affected or diseased part.

The mode of use can be appropriately selected while considering, for example, the body weight, the age, the sexuality, and the symptoms or condition of the patient. However, in the case of an adult, it is preferable to administer luliconazole in an amount of 0.01 to 5 g per day in ordinary cases. Reference can be made to the amount of use of luliconazole ordinarily used for the disease caused by any fungus. In the case of any disease caused by *Chlamydia*, *Trichomonas* or the like, luliconazole is also used in accordance therewith.

For example, in the case of any preparation for external use, it is possible to exemplify the application in an appropriate amount to the disease portion once or several times a day. It is preferable that the treatment as described above is performed every day. In the case of any internal medicine (agent), it is preferable to administer 500 mg to 2000 mg once or several times a day. In the case of any vaginal tablet, it is preferable to perform the adjustment so that the amount of luliconazole is 500 to 1500 mg and perform the administration intravaginally once per a day or several days. In the vaginal administration of luliconazole, it is possible to simultaneously treat protozoa such as *Trichomonas* and fungi such as *Candida*, which is preferred. In particular, in the case of the mixed infection (combined infection), the treatment can be performed by using one agent, which is preferred. Further, in the case of vaginitis (colpitis) caused by the simple infection of *Trichomonas*, it is possible to preventively avoid the fungal infection of *Candida* or the like simultaneously with the medical treatment, which is preferred.

It is possible to avoid the recurrence and the reinfection as described above by administering the pharmaceutical composition of the present invention for 1 week to 2 weeks after the quietness of symptoms. In such a mode, the pharmaceutical composition of the present invention has the preventive effect.

EXAMPLES

The present invention will be explained in further detail below as exemplified by Examples.

Example 1

150 mL of methanol was added to 10 g of luliconazole, followed by being heated at 60° C. and dissolved while performing stirring. 50 mL of water, which was heated to 70° C., was added thereto, and stirring and mixing were performed. After that, crystals were deposited while performing stirring by using cooling water at 5° C. Crystals were collected by means of filtration, followed by being dried while performing blowing for 48 hours at 40° C., and thus 6.4 g of crystals were obtained. When this sample was subjected to the powder X-ray diffraction measurement (RAD-A; produced by Rigaku Corporation, condition: X-ray source: CuKα, measurement temperature: room temperature, tube voltage: 40 kV, tube current: 20 mA, 2θ: 5 to 35°, step angle: 0.05°), the following peak characteristic result was revealed. FIG. 1 shows the result of the measurement of the powder X-ray diffraction measurement. It is appreciated that this sample is the luliconazole crystal of the present invention. The identification of plane was performed by making collation with the data of the single crystal X-ray structure analysis (name of machine type of apparatus: RU-H2R, name of manufacturer: Rigaku Corporation, condition: X-ray source: CuKα, measurement temperature: 26° C., tube voltage: 50 kV, tube current: 180 mA, 2θ max: 150.0°, structure analysis method: direct method (SHELX 86)). Various pieces of data of the single crystal X-ray structure analysis are shown below.

The peak intensity ratio is the ratio with respect to the sum total of the peak intensities of the diffraction peaks corresponding to (001) plane, (100) plane, (10-1) plane, (011) plane, (110) plane, (11-1) plane, (10-2) plane, (11-2) plane, (020) plane, (021) plane, (20-2) plane, (121) plane, (013) plane, (11-3) plane, and (221) plane. The same also holds in the following description.

Crystal system: monoclinic crystal;
Space group: $P2_1$;
Lattice constant:
a=9.0171(9) Å
b=8.167(1) Å
c=10.878(1) Å
β=95.917(9) °
R factor
R=0.046
$R_W$=0.047

TABLE 1

| 2θ (°); calculated value* | Identified plane | Peak intensity (cps**) | Peak intensity ratio (%) |
|---|---|---|---|
| 8.15 | (001) | 102 | 0.71 |
| 9.85 | (100) | 108 | 0.76 |
| 12.15 | (10-1) | 98 | 0.69 |
| 13.55 | (011) | 3612 | 25.28 |
| 14.65 | (110) | 65 | 0.45 |
| 16.30 | (11-1) | 1282 | 8.97 |
| 18.25 | (10-2) | 255 | 1.78 |
| 21.25 | (11-2) | 802 | 5.61 |
| 21.75 | (020) | 3100 | 21.70 |
| 23.25 | (021) | 2580 | 18.06 |
| 24.40 | (20-2) | 605 | 4.23 |
| 25.65 | (121) | 445 | 3.11 |
| 27.00 | (013) | 812 | 5.68 |
| 27.90 | (11-3) | 293 | 2.05 |
| 31.30 | (221) | 128 | 0.90 |

*calculated value of diffraction angle corresponding to each crystal plane calculated from single crystal X-ray structure analysis data
**count per second Example 2

The solvent for recrystallization was changed to 100 mL of methanol and 100 mL of water, and the operation was performed in the same manner as in Example 1 to obtain 7.1 g of crystals. Main peaks of this sample in the powder X-ray diffraction measurement are shown in Table 2 below. FIG. 1 shows the result of the powder X-ray diffraction measurement.

TABLE 2

| 2θ (°); calculated value | Identified plane | Peak intensity (cps) | Peak intensity ratio (%) |
|---|---|---|---|
| 8.15 | (001) | 90 | 0.71 |
| 9.85 | (100) | 123 | 0.97 |
| 12.15 | (10-1) | 198 | 1.56 |
| 13.55 | (011) | 1627 | 12.82 |
| 14.65 | (110) | 117 | 0.92 |
| 16.30 | (11-1) | 540 | 4.25 |
| 18.25 | (10-2) | 892 | 7.03 |
| 21.25 | (11-2) | 1487 | 11.71 |
| 21.75 | (020) | 3165 | 24.94 |
| 23.25 | (021) | 1635 | 12.88 |
| 24.40 | (20-2) | 775 | 6.11 |
| 25.65 | (121) | 647 | 5.10 |
| 27.00 | (013) | 825 | 6.50 |
| 27.90 | (11-3) | 413 | 3.26 |
| 31.30 | (221) | 158 | 1.25 |

Comparative Example 1

200 mL of ethyl acetate-n-hexane mixture solution (5:1) was added to 10 g of luliconazole, followed by being heated at 60° C. and dissolved while performing stirring. Crystals were deposited while performing stirring by using cooling water at 5° C. Crystals were collected by means of filtration, followed by being dried while performing blowing for 48 hours at 40° C., and thus 5 g of crystals were obtained. When this sample was subjected to the powder X-ray diffraction measurement (XRD-DSCII; produced by Rigaku Corporation, condition: X-ray source: CuKα, measurement temperature: room temperature, tube voltage: 40 kV, tube current: 40 mA, 2θ: 5 to 35°, step angle: 0.05°), the following peak characteristic result was revealed. FIG. 1 shows the result of the measurement of the powder X-ray diffraction measurement. It is appreciated that this sample has the specific crystal growth surface of (11-1) plane, and this sample is not the luliconazole crystal of the present invention. The identification of the plane was performed in the same manner as in Example 1.

TABLE 3

| 2θ (°); calculated value | Identified plane | Peak intensity (cps) | Peak intensity ratio (%) |
|---|---|---|---|
| 8.15 | (001) | 26 | 2.09 |
| 9.85 | (100) | 22 | 1.77 |
| 12.15 | (10-1) | 23 | 1.85 |
| 13.55 | (011) | 22 | 1.77 |
| 14.65 | (110) | 19 | 1.53 |
| 16.30 | (11-1) | 754 | 60.61 |
| 18.25 | (10-2) | 21 | 1.69 |
| 21.25 | (11-2) | 71 | 5.71 |
| 21.75 | (020) | 25 | 2.01 |
| 23.25 | (021) | 106 | 8.52 |
| 24.40 | (20-2) | 25 | 2.01 |
| 25.65 | (121) | 32 | 2.57 |
| 27.00 | (013) | 53 | 4.26 |
| 27.90 | (11-3) | 27 | 2.17 |
| 31.30 | (221) | 18 | 1.45 |

Example 3

The direct effect of luliconazole was investigated by using *Trichomonas vaginalis* (clinically isolated strain). That is, there were prepared a sample in which 5.08 mg of luliconazole of Comparative Example 1 recrystallized from n-hexane and ethyl acetate was added to "*Trichomonas* medium F" (produced by Fuji Pharma Co., Ltd.), a sample in which 5.08 mg of the crystal of Example 2 was added, and a sample (control) in which 5 µL of water was added. 200 mL of a culture of *Trichomonas vaginalis* of $3.93 \times 10^5$ individuals/mL was added thereto, followed by being cultured at 37° C. for 4 days, and the number of individuals of *Trichomonas* was counted on a hemocytometer. Results are shown in Table 4. A significant difference was confirmed at a significance level of not more than 1% among the three samples. Accordingly, it is appreciated that the crystal of the present invention is excellent in the solid-state reactivity.

TABLE 4

| | Average | SD |
|---|---|---|
| Example 2 | 256000 | 115238.9 |
| Comp. Ex. 1 | 376000 | 77974.35 |
| Control | 512000 | 76941.54 |

Example 4

A tablet was manufactured in accordance with a formulation shown in Table 5 below, and the hardness was measured. PTB311 (produced by Pharma Test GmbH) was used as a hardness meter. As for the tablet making condition, the tablet making was performed at a tablet making pressure of 1 ton/cm² by using a pestle and a mortar of 9 mmφ. In Comparative Example, the operation was performed in the same manner as described above by using the crystal (Comparative Example 1) obtained by performing the recrystallization with n-hexane-ethyl acetate. Table 6 shows an average of six samples. According to this result, it is appreciated that the crystal of the present invention has the high hardness, and it is possible to strictly separate or isolate the acid component and the basic component.

TABLE 5

| Component | % by mass |
|---|---|
| lactose | 50 |
| luliconazole | 50 |

TABLE 6

| Tablet | Hardness (N) |
|---|---|
| crystal of Example 2 | 73.7 ± 4.2 |
| crystal of Comp. Ex. 1 | 29.1 ± 3.0 |

Example 5

20 mg of each of the crystals was weighed, to which 2 ml of ethanol was added, followed by being stored by stationarily placed at 30° C. for 2 hours. The dissolution state was visually confirmed. Results are shown in Table 7. Accordingly, it is appreciated that the crystal of the present invention is easily dissolved in the polar solvent.

TABLE 7

| Crystal | Dissolution state |
|---|---|
| crystal of Example 1 | no crystal was found |
| crystal of Example 2 | no crystal was found |
| crystal of Comp. Ex. 1 | crystal was found at bottom |

INDUSTRIAL APPLICABILITY

The present invention can be applied to the pharmaceutical preparation.

What is claimed is:

1. A crystal of luliconazole recrystallized by a method comprising a step of dissolving luliconazole in a recrystallization solvent which is methanol which may contain water; and a step of recrystallizing luliconazole by stirring an obtained solution, wherein the crystal is characterized by crystal system of monoclinic crystal, space group of $P2_1$, lattice constant of a=9.0171(9) Å, b=8.167(1) Å, c=10.878(1) Å, β=95.917(9)°, R factor of R=0.046, $R_w$=0.047, and the crystal has such a crystal habit that (020) plane is a specific crystal growth surface:

luliconazole

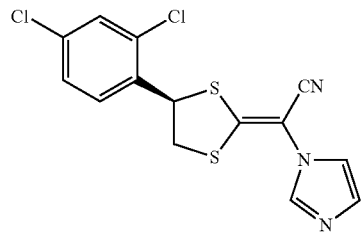

2. The crystal according to claim 1, wherein:
$I_{(020)}$, which is included in $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$, takes a first place or a second place as ranked in an order starting from those having a high peak intensity; and $I_{(020)}$ with respect to a sum total of $I_{(001)}$, $I_{(100)}$, $I_{(104)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ is not less than 20%, provided that:

peak intensities of diffraction peaks, which correspond to (001) plane, (100) plane, (10-1) plane, (011) plane, (110) plane, (11-1) plane, (10-2) plane, (11-2) plane, (020) plane, (021) plane, (20-2) plane, (121) plane, (013) plane, (11-3) plane, and (221) plane, are designated as $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ respectively in relation to the diffraction peaks detected in a range of 2θ=5 to 35° in powder X-ray diffraction measurement in which CuKα is used as an X-ray source.

3. The crystal according to claim 1, wherein recrystallization is performed by adding water to the obtained solution.

4. The crystal according to claim 3, wherein an amount of water is a volume of 10 to 60% with respect to the methanol.

5. The crystal according to claim 1, wherein the crystal has such a crystal habit that sulfur atom is arranged on a specific crystal growth surface.

6. An active pharmaceutical ingredient, comprising the crystal as defined in claim 1.

7. A pharmaceutical composition comprising the crystal as defined in claim 1 together with a component of medicament preparation.

8. The pharmaceutical composition according to claim 7, wherein a solid of the pharmaceutical composition is to be directly administered to an affected part.

9. The pharmaceutical composition according to claim 7, wherein the pharmaceutical composition is a vaginal tablet.

10. The pharmaceutical composition according to claim 7, wherein saccharide is comprised as a component of medicament preparation.

11. The pharmaceutical composition according to claim 10, wherein the saccharide is lactose.

12. A production method for producing a pharmaceutical composition, comprising a step of dissolving the crystal as defined in claim 1 in a polar solvent.

13. A pharmaceutical composition produced by the production method as defined in claim 12.

* * * * *

UNITED STATES PATENT AND TRADEMARK OFFICE
CERTIFICATE OF CORRECTION

PATENT NO. : 9,527,836 B2
APPLICATION NO. : 14/419864
DATED : December 27, 2016
INVENTOR(S) : Takaaki Masuda et al.

It is certified that error appears in the above-identified patent and that said Letters Patent is hereby corrected as shown below:

In the Specification

In Column 8 at Line 4, Change "2θ" to --2θ--.

In the Claims

In Column 14 at Line 22 (approx.), In Claim 2, change "$I_{(104)}$," to --$I_{(10-1)}$,--.

Signed and Sealed this
Twentieth Day of June, 2017

Joseph Matal
*Performing the Functions and Duties of the
Under Secretary of Commerce for Intellectual Property and
Director of the United States Patent and Trademark Office*